United States Patent
Choi et al.

(10) Patent No.: US 8,575,570 B2
(45) Date of Patent: Nov. 5, 2013

(54) SIMULTANEOUS ORTHOGONAL LIGHT SHEET MICROSCOPY AND COMPUTED OPTICAL TOMOGRAPHY

(75) Inventors: John M. Choi, Tujunga, CA (US); Thai V. Truong, Pasadena, CA (US); David S. Koos, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 222 days.

(21) Appl. No.: 13/217,580

(22) Filed: Aug. 25, 2011

(65) Prior Publication Data

US 2012/0049087 A1　Mar. 1, 2012

Related U.S. Application Data

(60) Provisional application No. 61/377,052, filed on Aug. 25, 2010.

(51) Int. Cl.
　　*F21V 9/16*　　(2006.01)
(52) U.S. Cl.
　　USPC .................. 250/459.1; 359/385; 359/368
(58) Field of Classification Search
　　USPC ............. 250/459.1; 359/368, 385, 398, 708, 359/739; 356/432
　　See application file for complete search history.

(56) References Cited

U.S. PATENT DOCUMENTS

| | | | |
|---|---|---|---|
| 6,020,591 A | 2/2000 | Harter et al. | |
| 6,844,963 B2 | 1/2005 | Iketaki et al. | |
| 6,856,712 B2 | 2/2005 | Fauver et al. | |
| 7,282,716 B2 | 10/2007 | Prelewitz et al. | |
| 7,307,802 B2 | 12/2007 | Unger | |
| 7,554,726 B2 * | 6/2009 | Ulrich et al. | 359/385 |
| 7,787,179 B2 * | 8/2010 | Lippert et al. | 359/385 |
| 8,441,633 B2 | 5/2013 | Truong et al. | |
| 2006/0011804 A1 | 1/2006 | Engelmann et al. | |
| 2006/0250690 A1 * | 11/2006 | Ulrich et al. | 359/385 |
| 2007/0087284 A1 | 4/2007 | Fleming et al. | |
| 2007/0109633 A1 * | 5/2007 | Stelzer | 359/385 |
| 2007/0148760 A1 | 6/2007 | Klesel et al. | |

(Continued)

FOREIGN PATENT DOCUMENTS

| | | |
|---|---|---|
| DE | 102007047461 A1 | 4/2009 |
| EP | 1207387 A1 | 5/2002 |

(Continued)

OTHER PUBLICATIONS

Darrell et al., "Weighted filtered backprojection for quantitative fluorescence optical projection tomography", Physics in Medicine and Biology, 2008, vol. 53, pp. 3863-3881.

(Continued)

*Primary Examiner* — David Porta
*Assistant Examiner* — Taeho Jo
(74) *Attorney, Agent, or Firm* — KPPB LLP

(57) ABSTRACT

An apparatus for and method of performing orthogonal light sheet microscopy (OLM) and computer optical tomography (COT) simultaneously in a single device are provided. The dual-mode imaging microscope allows for the use of both OLM and COT in a single instrument. This dual-mode device will allow researchers to have access to both types of microscopy, allowing access to the widest possible selection of samples, and improved imaging results. In addition, the device will reduce the high costs and space requirements associated with owning two different imagers (OLM and COT).

42 Claims, 12 Drawing Sheets

(56) References Cited

U.S. PATENT DOCUMENTS

| | | | |
|---|---|---|---|
| 2008/0043786 A1 | 2/2008 | Wilhelm et al. | |
| 2008/0116392 A1 | 5/2008 | Brooker | |
| 2008/0218850 A1* | 9/2008 | Power | 359/385 |
| 2009/0027769 A1 | 1/2009 | Saito et al. | |
| 2009/0028503 A1 | 1/2009 | Garrett et al. | |
| 2009/0225413 A1* | 9/2009 | Stelzer et al. | 359/385 |
| 2010/0067102 A1 | 3/2010 | Yokoi et al. | |
| 2010/0075361 A1 | 3/2010 | Mattoussi et al. | |
| 2010/0078576 A1 | 4/2010 | Ntziachristos et al. | |
| 2010/0276608 A1 | 11/2010 | Liu et al. | |
| 2010/0309548 A1 | 12/2010 | Power et al. | |
| 2011/0115895 A1* | 5/2011 | Huisken | 348/79 |
| 2011/0122488 A1 | 5/2011 | Truong et al. | |
| 2011/0134521 A1 | 6/2011 | Truong et al. | |
| 2012/0141981 A1 | 6/2012 | Pantazis et al. | |

FOREIGN PATENT DOCUMENTS

| | | | |
|---|---|---|---|
| WO | 9107651 A1 | 5/1991 | |
| WO | 2009043473 A1 | 4/2009 | |
| WO | 2009100830 A1 | 8/2009 | |
| WO | 2009124700 A1 | 10/2009 | |
| WO | 2010014244 A2 | 2/2010 | |
| WO | 2011059826 A2 | 5/2011 | |
| WO | 2011059833 A2 | 5/2011 | |
| WO | 2011059826 A2 | 9/2011 | |
| WO | 2012027542 A2 | 3/2012 | |
| WO | 2012027542 A3 | 3/2012 | |

OTHER PUBLICATIONS

Keller et al, "Reconstruction of Zebrafish Early Embryonic Development by Scanned Light Sheet Microscopy", Science, Nov. 14, 2008, vol. 322, pp. 1065-1069.
International Search Report and Written Opinion for International Application PCT/US2011/049089; mailed Mar. 26, 2012, 7 pgs.
Abbott et al., "Biology's new dimension", Nature, Aug. 21, 2003, vol. 424, pp. 870-872.
Cassidy et al., "Molecular Imaging Perspectives", Journal of the Royal Society Interface, vol. 40, 2005, pp. 1-12.
Darrell et al., "Improved fluorescence optical projection tomography reconstruction", SPIE, 2008, 4 pgs.
Darrell et al., "Weighted filtered backprojection for quantitative fluorescence optical projection tomography", Physics in Medicine and Biology, 2008, vol. 53, pp. 3863-3881.
Fuchs et al., "Thin laser light sheet microscope for microbial oceanography", Optics Express, Jan. 28, 2002, vol. 10, No. 2, pp. 145-154.
Keller et al., "Life sciences require third dimension", Current Opinion in Cell Biology, 2006, vol. 18, pp. 117-124.
Keller et al., "Reconstruction of Zebrafish Early Embryonic Development by Scanned Light Sheet Microscopy", Science, Nov. 14, 2008, vol. 322, pp. 1065-1069.
Santi et al., "Thin-sheet laser imaging microscopy for optical sectioning of thick tissues", BioTechniques, Short Technical Reports, Apr. 2009, vol. 46, pp. 287-294.
Sharpe, "Optical Projection Tomography", Annu. Rev. Biomed. Eng., 2004, vol. 6, pp. 209-228.
Sharpe et al., "Optical Projection Tomography as a Tool for 3D Microscopy and Gene Expression Studies", Science, 2002, vol. 296, pp. 541-545.
Swoger et al., "Multi-view image fusion improved resolution in three-dimensional microscopy", Optics Express, Jun. 2007, vol. 15, No. 13, 14 pgs.
Truong et al., "Deep and fast live imaging with two-photon scanned light-sheet microscopy", Nature Methods, Advance Online Publication, 2011, pp. 1-40.
Walls et al., "Correction of artefacts in optical projection tomography", Physics in Medicine and Biology, 2005, vol. 50, pp. 4645-4665.
Walls et al., "Resolution improvement in emission optical projection tomography", Phys. Med. Biol., 2007, vol. 52, pp. 2775-2790.
Bewersdorf et al., "Multifocal multiphoton microscopy", Optics Letters, May 1, 1998, vol. 23, No. 9, pp. 655-657.
Bousso, "Real-time imaging of T-cell development", Current Opinion in Immunology, 2004, vol. 16, pp. 400-405.
Breuninger et al., "Lateral modulation boosts image quality in single plane illumination fluorescence microscopy", Optics Letters, Jun. 1, 2007, vol. 32, No. 13, pp. 1938-1940.
Campagnola et al., "Second-harmonic imaging microscopy for visualizing biomolecular arrays in cells, tissues and organisms", Nature Biotechnology, Nov. 2003, vol. 21, No. 11, pp. 1356-1360.
Denk et al., "Two-Photon Laser Scanning Fluorescence Microscopy", Reports, Apr. 6, 1990, vol. 248, No. 4951, pp. 73-76.
Dodt et al., "Ultramicroscopy: three-dimensional visualization of neuronal networks in the whole mouse brain", Nature Methods, Apr. 2007, Vo. 4, No. 4, pp. 331-336.
Fahrbach et al., "Microscopy with self-reconstructing beams", Nature Photonics, Nov. 2010, vol. 4, pp. 780-785.
Friedl, "Immunological techniques Dynamic imaging of the immune system", Current Opinion in Immunology, 2004, vol. 16, pp. 389-393.
Holekamp et al., "Fast Three-Dimensional Fluorescence Imaging of Activity in Neural Populations by Objective-Coupled Planar Illumination Microscopy", Neuron, Mar. 13, 2008, vol. 57, pp. 661-672.
Huisken et al., "Even fluorescent excitation by multidirectional selective plane illumination microscopy", Optics Letters, Sep. 1, 2007, vol. 32, No. 17, pp. 2608-2610.
Huisken et al., "Optical Sectioning Deep Inside Live Embryos by Selective Plane Illumination Microscopy", Science, 2004, vol. 305, pp. 1007-1009.
Huisken et al., "Selective plane illumination microscopy techniques in developmental biology", Development, 2009, vol. 136, pp. 1963-1975.
Ji et al., "Adaptive optics via pupil segmentation for high-resolution imaging in biological tissues", Nature Methods, Feb. 2010, vol. 7, No. 2, pp. 141-150.
Ji et al., "Advances in the speed and resolution of light microscopy", Current Opinion in Neurobiology, 2008, vol. 18, pp. 605-616.
Ji et al., "High-speed, low-photodamage nonlinear imaging using passive pulse splitters", Nature Methods, Feb. 2008, vol. 5, No. 2, pp. 197-202.
Keller et al., "Fast, high-contrast imaging of animal development with scanned light sheet-based structured-illumination microscopy", Nature Methods, Advance Online Publication, Jul. 4, 2010, pp. 1-9.
Keller et al., "Quantitative in vivo imaging of entire embryos with Digital Scanned Laser Light Sheet Fluorescence Microscopy", Current Opinion in Neurobiology, 2009, vol. 18, pp. 1-9.
Kerr et al., "Imaging in vivo: watching the brain in action", Nature Review, Neuroscience, Mar. 2008, vol. 9, pp. 195-205.
Mavrakis et al., "Lighting up developmental mechanisms: how fluorescence imaging heralded a new era", Development, 2010, vol. 137, pp. 373-387.
McMahon et al., "Dynamic Analyses of Drosophila Gastrulation Provide Insights into Collective Migration", Science, Dec. 5, 2008, vol. 322, pp. 1546-1550.
Mertz, "Nonlinear microscopy: new techniques and applications", Current Opinion in Neurobiology, 2004, vol. 14, pp. 610-616.
Olivier et al., "Cell Lineage Reconstruction of Early Zebrafish Embryos Using Label-Free Nonlinear Microscopy", Science, Aug. 20, 2010, vol. 329, pp. 967-971.
Olivier et al., "Two-photon microscopy with simultaneous standard and extended depth of file using a tunable acoustic gradient-index lens", Optics Letters, Jun. 1, 2009, vol. 34, No. 11, pp. 1684-1686.
Palero et al., "A simple scanless two-photon fluorescence microscope using selective plane illumination", Optics Express, Apr. 12, 2010, vol. 18, No. 8, pp. 8491-8498.
Pantazis, et al., "Second harmonic generating (SHG) nanoprobes for in vivo imaging", PNAS, Aug. 17, 2010, vol. 107, No. 33, pp. 14535-14540.
Preibisch et al., "Software for bead-based registration of selective plan illumination microscopy data", Nature Methods, Jun. 2010, vol. 7, No. 6, 20 pgs.

(56) References Cited

OTHER PUBLICATIONS

Provenzano et al., "Shining new light on 3D cell motility and the metastatic process", Trends in Cell Biology, 2009, vol. 19, No. 11, pp. 638-648.

Pu et al., "Nonlinear Optical Properties of Core-Shell Nanocavities for Enhanced Second-Harmonic Generation", Physical Review Letters, May 21, 2010, vol. 104, pp. 2074021-2074024.

Schonle et al., "Heating by absorption in the focus of an objective lens", Optics Letters, Mar. 1, 1998, vol. 23, No. 4, pp. 325-327.

Supatto et al., "Quantitative imaging of collective cell migration during drosophila gastrulation: multiphoton microscopy and computational analysis", Nature Protocols, 2009, vol. 4, No. 10, pp. 1397-1412.

Vermot et al., "Fast fluorescence microscopy for imaging the dynamics of embryonic development", HFSP Journal, Jun. 2008, vol. 2, No. 3, pp. 143-155.

Verveer et al., "High-resolution three-dimensional imaging of large specimens with light sheet-based microscopy", Nature Methods, Apr. 2007, vol. 4, No. 4, pp. 311-313.

Voie et al., "Orthogonal-plan fluorescence optical sectioning: three-dimensional imaging of macroscopic biological specimens", Journal of Microscopy, Jun. 1993, vol. 170, Pt. 3, pp. 229-236.

Volodymyr et al., "SLM microscopy: scanless two-photon imaging and photostimulation with spatial light modulators, 2008, Frontiers in Neural Circuits", vol. 2, Article 5, pp. 1-14.

Williams et al., "Interpreting Second-harmonic Generation Images of Collagen I Fibrils", Biophysical Journal, Feb. 2005, vol. 88, pp. 1377-1386.

Zipfel et al., "Nonlinear magic: multiphoton microscopy in the biosciences", Nature Biotechnology, Nov. 2003, vol. 21, No. 11, pp. 1369-1377.

* cited by examiner

PRIOR ART

PRIOR ART

SIMULTANEOUS ORTHOGONAL LIGHT SHEET MICROSCOPY AND COMPUTED OPTICAL TOMOGRAPHY

CROSS-REFERENCE TO RELATED APPLICATIONS

The current application claims priority to U.S. Provisional Application No. 61/377,052, filed, Aug. 25, 2010, the disclosure of which is incorporated herein by reference.

STATEMENT OF FEDERAL FUNDING

This invention was made with government support under EY018241 and HG004071 awarded by the National Institutes of Health and with government support under NB10852883 awarded by the National Science Foundation. The government has certain rights in the invention.

FIELD OF THE INVENTION

The present invention relates generally to imaging microscopes and microscopy, and more specifically to a microscope that allows for the simultaneous operation of the device to perform both orthogonal light sheet microscopy (OLM) and computed optical tomography (COT).

BACKGROUND OF THE INVENTION

For certain aspects of biology, three-dimensional (3D) imaging of large samples is necessary, such as, for example, in examining the organization of tissue, in mapping gene expression within a tissue structure, in looking at network interactions, and in studying interconnectivity. Advanced optical microscopy techniques offer unique opportunities to investigate these biological structures and processes in vivo. The ability to image tissues or organisms in three dimensions (3D) and/or over time (4D imaging) permits a wide range of applications in neuroscience, immunology, cancer research, and developmental biology. (See, e.g., Mertz, Curr. Opin. Neurobiol. 14, 610-616, (2004); Kerr, J. N. D. & Denk, W., Nature Reviews Neuroscience 9, 195-205, (2008); Friedl, P., Current Opinion in Immunology 16, 389-393, (2004); Bousso, P., Current Opinion in Immunology 16, 400-405, (2004); Provenzano, P. P., et al., Trends in Cell Biology 19, 638-648, (2009); Keller, P. J., et al., Science 322, 1065-1069 (2008); McMahon, A., et al., Science 322, 1546-1550 (2008); and Mavrakis, M., et al., Development 137, 373-387, (2010), the disclosures of each of which are incorporated herein by reference.) Fundamental light-matter interactions, such as light scattering, absorption, and photo-induced biological toxicity, set the limits on the performance parameters of various imaging technologies in terms of spatial resolution, acquisition speed, and depth penetration (how deep into a sample useful information can be collected). Often, maximizing performance in any one of these parameters necessarily means degrading performance in the others. (See, e.g., Ji, N., et al., Curr. Opin. Neurobiol. 18, 605-616, (2008) and Vermot, J., et al., HFSP Journal 2, 143-155 (2008), the disclosures of each of which are incorporated herein by reference.)

An example of the limitations of the current technique can be seen in conventional light sheet (LISH) or Orthogonal Light Sheet (OLM) microscopy. LISH/OLM microscopy is a century-old technology that has seen much development and refinement in recent years, under names ranging from Thin Laser light Sheet Microscopy (TLSM), Selective Plane Illumination Microscopy (SPIM) (FIG. 1A, high-speed imaging of live zebrafish heart), Objective Coupled Planar Illumination (OCPI) (FIG. 1B, high-speed calcium imaging of neurons), ultramicroscopy (FIG. 1C, blood vessel system of mouse embryo), and Digital Scanned Laser Light Sheet Fluorescence Microscopy (DSLM) (FIG. 1D, in toto imaging of developing zebrafish embryo), among others. (See, e.g., Siedentopf, H. & Zsigmondy, R., Ann. Phys.-Berlin 10, 1-39 (1902); Voie, A. H., et al., J. Microsc.-Oxf. 170, 229-236 (1993); Fuchs, E., et al., Opt. Express 10, 145-154 (2002); Huisken, J., et al., Science 305, 1007-1009 (2004); Holekamp, T. F., et al., Neuron 57, 661-672 (2008); Dodt, H. U. et al., Nat. Methods 4, 331-336 (2007); Huisken, J. & Stainier, D. Y. R., Development 136, 1963-1975 (2009); and Keller, P. J. & Stelzer, E. H. K., Curr. Opin. Neurobiol. 18, 624-632 (2008), the disclosures of each of which are incorporated herein by reference.)

In LISH or OLM, as it will be referred to herein, (FIG. 1E) a planar sheet of light is used to illuminate the sample, generating fluorescence signal over a thin optical section of the sample, which is then imaged from the direction orthogonal to the light sheet with a wide-field imaging camera. Axial sectioning results from the thinness of the light sheet, while lateral resolution is determined by the detection optics. The orthogonal geometry between the illumination and detection pathways of OLM, compared to the collinear geometry of conventional microscopes, not only enables higher imaging speed due to the parallel image collection (millions of voxels can be imaged simultaneously), but also reduces phototoxicity since only a single focal plane of the sample is illuminated at a time. The depth penetration of OLM into scattering biological tissue, however, is limited (only slightly better than CLSM), due to (i) the imaging requirement of the wide-field detection that requires ballistic fluorescence photons only and scattered photons would degrade the image quality, and (ii) the light sheet is spatially degraded beyond its original thinness due to scattering, as it is focused deep inside an optically heterogeneous sample.

Although OLM offers a great deal of promise, the need for orthogonal illumination means that all fluorescence imaging is done with scattered photons or photons from the fluorophore. Most of the excitation photons do not enter the imaging objective, nor does OLM use the information inherent in the transmitted or absorbed photons. Ideally, an imaging microscope would use the full measure of excitation photons being input into the system, thereby allowing access to the widest possible selection of samples and obtaining the largest amount of structural data. However, currently there are no microscopes or other imaging devices that can do both OLM microscopy and utilize the data generated by the non-orthogonal excitation photons.

Accordingly, it would be advantageous to develop an optical microscope that allows for the simultaneous use of both orthogonally scattered photons or fluorescence, and the in-plane absorbed or transmitted photons to provide new combinations of imaging capabilities heretofore unobtainable with conventional OLM microscopy techniques.

SUMMARY OF THE INVENTION

The present invention is directed to a microscope device that may collect data both from photons in-plane and orthogonal to the axis of the excitation.

In one embodiment, the invention is directed to a dual-mode imaging microscope that includes:

at least one excitation source, the excitation source being capable of producing an excitation beam, and being disposed such that the excitation is directed along at least one excitation beam path;

a sample holder in optical communication with the excitation source such that a sample contained therein is excited by the excitation beam;

an excitation optic capable of producing from the excitation beam a substantially two-dimensional sample excitation region having an effectively uniform excitation intensity which extends in the direction of an excitation axis of the excitation beam path and transversely thereto and intersects with at least a portion of the sample holder along a pre-determined path;

a tomography detector configured to detect an excitation generated signal contrast from the sample holder, the tomography detector being disposed such that the axis of detection of at least one tomography detector is substantially collinear to the excitation beam;

a light sheet microscope detector configured to detect an excitation generated signal contrast from the sample excitation region, the light sheet microscope detector being disposed such that the axis of detection of at least one light sheet detector is substantially orthogonal to the sample excitation region;

wherein the angular orientation of the excitation region relative to the sample holder may be varied about the axis of the sample holder, and wherein the position of the excitation region relative to the sample holder may be varied along the light sheet detector axis; and wherein the axis about which the angular orientation may be varied is not parallel to the excitation beam path.

In another embodiment, the axis of the sample and the axis of the light sheet detector are one of either parallel or perpendicular.

In still another embodiment, the excitation source is a continuous-wave laser producing an excitation beam in the visible wavelength range, said excitation source being capable of inducing 1-photon-excited signal contrast for imaging, and wherein said signal contrast is proportional to $I^n$, where I is the instantaneous intensity of the excitation beam at the sample excitation region and n is the number of photons involved in the excitation, and where n is 1.

In yet another embodiment, the at least one excitation source is capable of producing an excitation beam of high enough intensity to induce sufficient levels of multi-photon excitation to produce signal contrast for imaging, and wherein said signal contrast is proportional to $I^n$, where I is the instantaneous intensity of the excitation beam at the sample excitation region and n is the number of photons involved in the multi-photon excitation, and where n is greater than 1.

In still yet another embodiment, the excitation source is a pulsed near-infrared laser selected from the group consisting of lasers having pulse durations in the range of nanosecond, picoseconds, and femtosecond.

In still yet another embodiment, the detected signal contrast is selected from the group consisting of 1-photon-excited fluorescence, Rayleigh scattering, Raman-shifted scattering, second harmonic generation, third harmonic generation, sum frequency generation, and stimulated Raman scattering.

In still yet another embodiment, the at least one excitation source is capable of creating two coaxial and oppositely aligned excitation beams, such that said sample excitation region is formed from the overlap of said two excitation beams.

In still yet another embodiment, the numerical aperture of at least the excitation optic is adjustable. In one such embodiment, the adjustable numerical aperture comprises a beam expander with an adjustable expanding ratio.

In still yet another embodiment, the numerical aperture of at least the excitation optic is anisotropic along at least two axes of said excitation beam.

In still yet another embodiment, focal volume engineering is applied to the excitation beam to optimize for light sheet imaging. In one such embodiment, focal volume engineering is implemented using one of the techniques selected from the group consisting of having the numerical aperture of the excitation optic being anisotropic along at least two axes of said excitation beam, and having the excitation beam be a Bessel beam. In another such embodiment, the focal engineering is implemented by one or more optical elements selected from the group consisting of two orthogonally oriented sequential adjustable slit apertures, a plurality of independently expanding beam expanders, liquid crystal spatial light modulators, digital micromirror device spatial light modulators, and axiconic lens.

In still yet another embodiment, the excitation beam is one of either substantially planar-shaped or linearly-shaped. In one such embodiment, the excitation beam is linearly-shaped, and wherein excitation optic is configured to focus and laterally scan said excitation beam along a desired axis of the excitation beam path to produce the substantially two-dimensional sample excitation region.

In still yet another embodiment, the microscope incorporates a technique selected from the group consisting of Orthogonal Plane Fluorescence Optical Sectioning (OPFOS), Selective Plane Illumination Microscopy (SPIM), Ultramicroscopy, and Digital Scanned Laser Light Sheet Fluorescence Microscopy (DSLM).

In still yet another embodiment, the sample holder is moveable relative to the sample excitation region.

In still yet another embodiment, the sample excitation region is moveable relative to the sample holder.

In still yet another embodiment, the sample contains at least one type of marker selected from the group consisting of absorptive, transmissive, reflective, fluorescent, infrared, and near infrared.

In still yet another embodiment, the sample is fixed within the sample holder in a sample matrix.

In still yet another embodiment, the tomography detector detects a signal contrast selected from the group consisting of transmission, absorption and reflection.

In still yet another embodiment, the light sheet detector detects a signal contrast selected from the group consisting of scattered and emissive.

The invention is also directed to a method of imaging an object using a dual-mode imaging microscope comprising:
  producing an excitation beam, and directing the excitation beam along an excitation beam path;
  placing a sample within the optical path of the excitation beam to generate at least one signal contrast;
  producing from the excitation beam a substantially two-dimensional sample excitation region having an effectively uniform excitation intensity which extends in the direction of an excitation axis of the excitation beam path and transversely thereto and intersects with at least a portion of the sample;
  detecting the signal contrast along a tomography detection axis that is substantially collinear to the excitation beam;
  detecting the signal contrast along a light sheet detection axis that is substantially orthogonal to the sample excitation region; and varying the angular orientation of the excitation region relative to the sample about the axis of the sample and varying the position of the excitation region relative to the sample along the light sheet detector axis to obtain data along a specific angular and positional axis of the sample, wherein the axis about which the angular orientation may be varied is not parallel to the excitation beam path; and repeating the steps of producing, detecting and varying until sufficient angular and positional data has been obtained.

In one embodiment, the axis of the sample and the axis of the light sheet detector are one of either parallel or perpendicular.

In another embodiment, the angular orientation of the excitation region relative to the sample is rotated through at least 180 degrees. In another such embodiment, the angular orientation of the excitation region relative to the sample is rotated through at least 360 degrees. In still another such embodiment, the angular orientation of the excitation region relative to the sample is varied in steps of no greater than 1 degree.

In yet another embodiment, the excitation region is scanned across the sample at multiple points along the light sheet detector axis at each different angular orientation.

In still another embodiment, the sample is moved relative to the sample excitation region.

In still yet another embodiment, the sample excitation region is moved relative to the sample.

In still yet another embodiment, at least one type of marker selected from the group consisting of absorptive, transmissive, reflective, fluorescent, infrared, and near infrared is inserted in the sample. In another such embodiment, the sample is fixed within a sample matrix.

In still yet another embodiment, the signal contrast detected along the tomography detection axis is selected from the group consisting of transmission, absorption and reflection.

In still yet another embodiment, the signal contrast detected along the light sheet detection axis is selected from the group consisting of scattered and emissive.

In still yet another embodiment, the method further includes focusing and laterally scanning the excitation beam along a desired axis of the excitation beam path to produce a substantially two-dimensional sample excitation region having an effectively uniform excitation intensity which extends in the direction of an excitation axis of the excitation beam path and transversely thereto and intersects with at least a portion of the sample.

In still yet another embodiment, at least one excitation beam is produced with a continuous-wave laser producing an excitation beam in the visible wavelength range, said excitation source being capable of inducing 1-photon-exicted signal contrast for imaging, and wherein said signal contrast is proportional to $I^n$, where I is the instantaneous intensity of the excitation beam at the sample excitation region and n is the number of photons involved in the excitation, and where n is 1

In still yet another embodiment, the at least one excitation beam is of high enough intensity to induce sufficient levels of multi-photon excitation to produce signal contrast for imaging, and wherein said signal contrast is proportional to $I^n$, where I is the instantaneous intensity of the excitation beam at the sample excitation region and n is the number of photons involved in the multi-photon excitation, and where n is greater than 1

In still yet another embodiment, the excitation beam is produced via a pulsed near-infrared laser selected from the group consisting of lasers having pulse durations in the range of nanosecond, picoseconds, and femtosecond.

In still yet another embodiment, detecting the signal contrast includes using a detection technique selected from the group consisting of fluorescence, second harmonic generation, third harmonic generation, sum frequency generation, and stimulated Raman scattering.

In still yet another embodiment, the method includes forming at least two coaxial and oppositely aligned excitation beams, such that said sample excitation region is formed from the overlap of said two excitation beams.

In still yet another embodiment, the focusing of the excitation beam further includes adjusting the numerical aperture of a focusing optic.

In still yet another embodiment, the focusing of the excitation beam further includes anisotropically adjusting the numerical aperture of a focusing optic such that the excitation beam is anisotropic along at least two axes.

BRIEF DESCRIPTION OF THE DRAWINGS

These and other features and advantages of the present invention will be better understood by reference to the following detailed description when considered in conjunction with the accompanying drawings and data, wherein.

DETAILED DESCRIPTION OF THE INVENTION

The current invention is directed to a novel three-dimensional volume imaging microscope capable of using a single light sheet excitation source to derive information both from orthogonal scattering or fluorescence, as well as from the in-plane absorption or transmission. The microscope device uses a special optical arrangement that allows for the simultaneous use of OLM and COT.

COT Technique

Figure 1A:
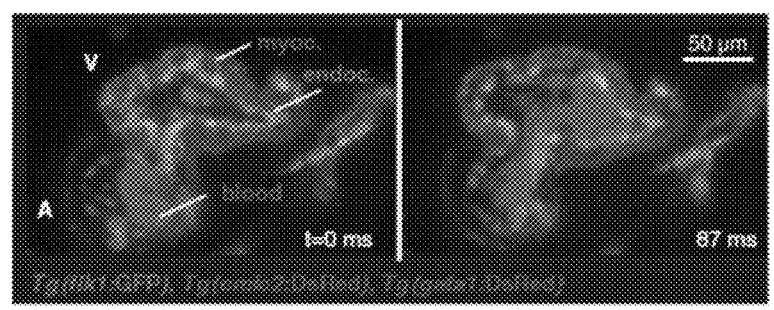
FIGS. 1A to 1D provide images and data form experiments taken using: (A) SPIM; (B) ultramicroscopy; (C) OCIP; and (D) DSLM.
Figure 1B:
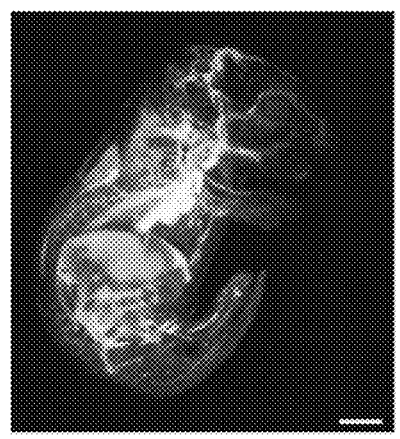
Figure 1C:
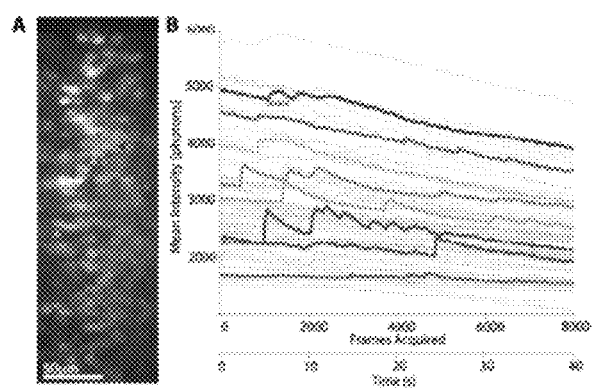
Figure 1D:
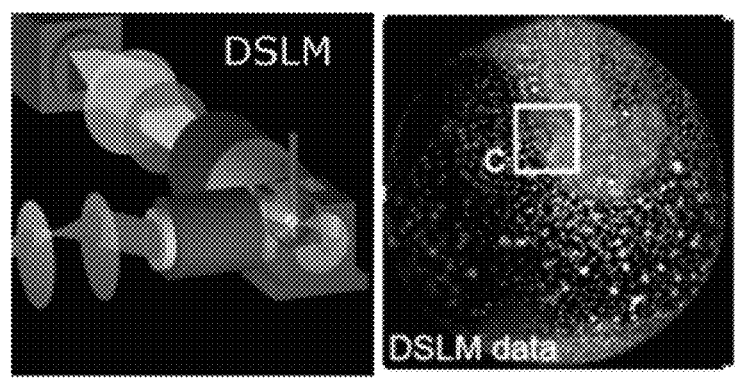
Figure 1E:
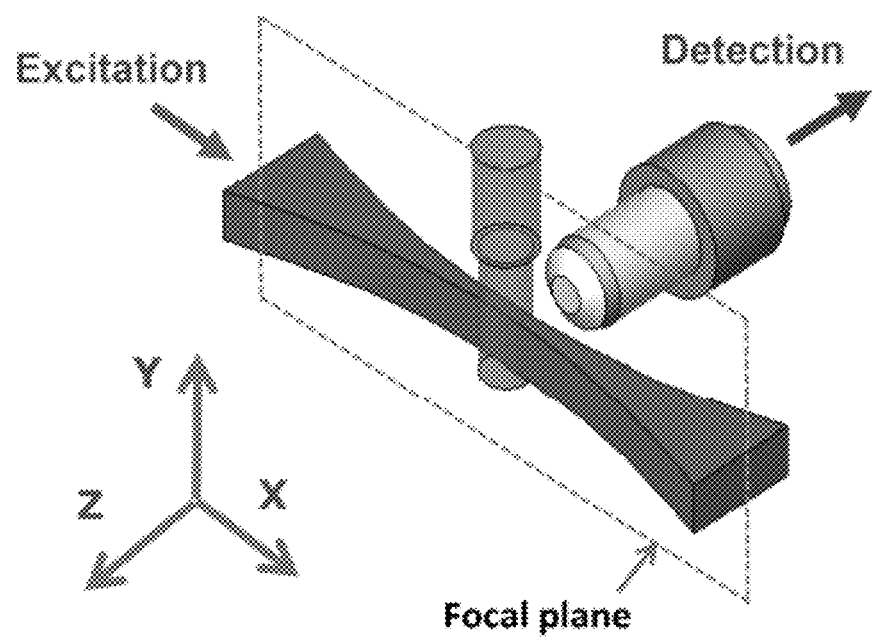
FIG. 1E provides a schematic of a conventional LISH/OLM microscope.
Figure 2A:
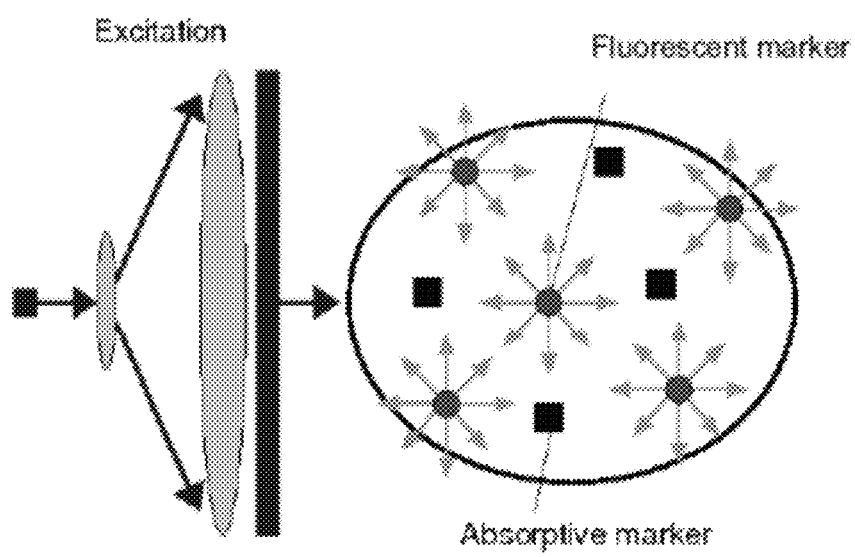
FIG. 2A provides a schematic of a conventional COT system showing illumination of the entire sample simultaneously.

Computed Optical Tomography (COT) techniques, such as Optical Projection Tomography (OPT), is a standard way to collect 3-dimensional (3D) images of biological samples. As shown in FIG. 2A, which shows a simplified schematic of a conventional COT microscope, in COT the illumination light is shined onto the entire sample, and detection of emitted light is done in the transmitted direction, collinear with the illumination direction. COT creates a digital volumetric model of an object by reconstructing images made from the light transmitted and scattered through an object. There are also several variants of optical tomography, including optical time-of-flight sampling, which attempts to distinguish transmitted light from scattered light using either time-resolved or frequency domain data, and fluorescence tomography, in which the fluorescence signal transmitted through the tissue is normalized by the excitation signal transmitted through the tissue. It should be understood that any of these conventional COT techniques may be incorporated into the device of the current invention.

COT is excellent for structural imaging, and in particular at identifying features at the tissue and organ level, including morphology and shape. COT is also good for use with chromogenic reporters such as diaminobenzidine, LacZ induced deposition of Xgal (X-gal (also abbreviated BCIG for bromo-chloro-indolyl-galactopyranoside) and Xgal-like variants such as Bluo-gal (halogenated indolyl-galactoside) and Salmon-gal (6-Chloro-3-indolyl-D-galactopyranoside), charcoal., etc., and for imaging absorbing dyes for labeling organs or subsets of tissue types. However, COT cannot provide quantitative fluorescence results without the use of complex modeling and algorithms, and even then the final image may contain artifacts. (See, Darrell, H., et al., Phys. Med. Biol. 53: 3863-3881 (2008); and Darrell, J. Swoger, et al., SPIE Newsroom DOI: 10.1117/2.1200810.1329 (6 Nov. 2008), the disclosures of which are incorporated herein by reference.) Furthermore, because COT is confocal, it is unsuitable for use with colored dyes. (J. Sharpe, et al., Science 296: 541-545 (2002), the disclosure of which is incorporated herein by reference.) Finally, COT does not provide subcellular resolution. In fact, because COT resolution is limited by the assumption of parallel line integrals and a depth of field dictated by mode curvature, its resolution is typically on the order of 5-10 μm, the Rayleigh length of Gaussian beams. (J. Sharpe, Annu. Rev. Miomed. Eng. 6: 209-228 (2004); and P. J. Cassidy and G. K. Radda, J. R. Soc. Interface 2: 133-144 (2005), the disclosures of which are incorporated herein by reference.

OLM Microscopy

Figure 2B:
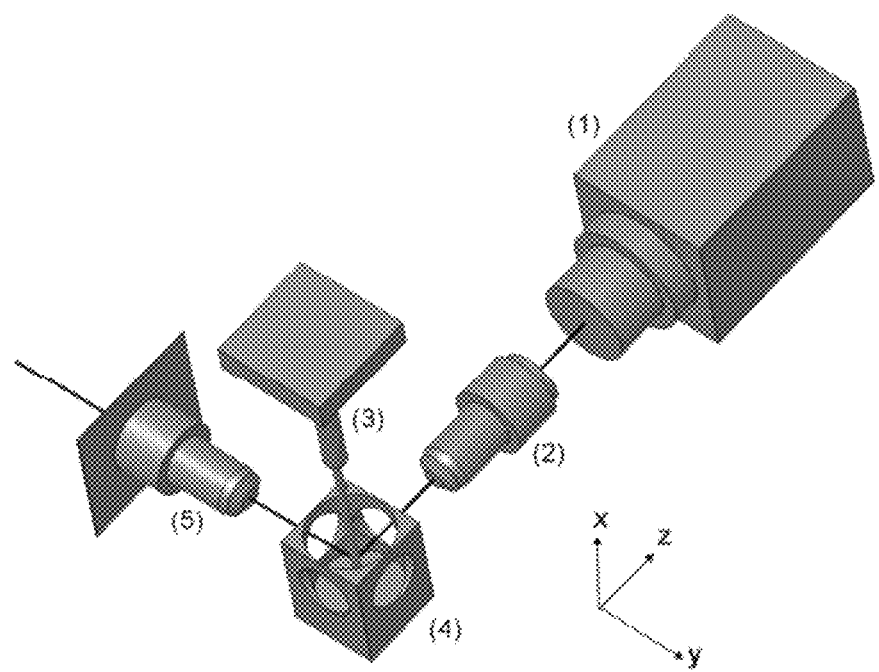
FIG. 2B provides a schematic of a conventional OLM system.

A schematic of a conventional OLM microscope is provided in FIG. 2B. The basic OLM apparatus, as shown, includes an illumination objective (5) positioned along a first axis of a sample chamber (4). The sample chamber houses the sample to be imaged, which is attached to a holder and controller (3), preferably allowing control in x, y, z, and theta (rotational). A detection objective (2), and imaging device, such as, for example, a camera (1) are positioned in line of sight to the sample chamber along a second axis that is orthogonal to the first illumination axis. Black solid lines depict the optical axis of the illumination and detection beams, going through (5) and (2), respectively. Not shown are the mechanical supports of the system. (For a detailed description of an OLM or LISH microscope see, U.S. Pat. Pub. No. 2009/0225413, the disclosure of which is incorporated herein by reference.)

As shown in the above schematic, OLM is a microscopy technique where the illumination is done from the side of the sample, creating a diffraction-limited planar sheet of light going across the sample. (See, J. Huisken and D. Y. R. Stainier, Development 136, 1963-1975 (2009), the disclosure of which is incorporated herein by reference.) Detection of the emitted light is done at 90 degrees from the illumination direction, orthogonal to the light sheet. Z-sectioning is achieved since only one diffraction-limited plane is illuminated at a time. The sample may be scanned through the plane (or inversely the plane could be scanned through the sample) to allow coverage of the whole sample volume.

OLM microscopy differs from COT microscopy in the geometry of the illumination and detection optical pathways. COT microscopy, which is a widely used imaging technology, uses a collinear geometry between the illumination and detection pathways. (See, e.g., Pawley, Handbook of Confocal Microscopy, $3^{rd}$ Edition, New York: Springer (2006), the disclosure of which is incorporated herein by reference.) This results in some inherent advantages for OLM microscopy. In particular, because of the orthogonal geometry between the illumination and detection directions, the lateral extent of the illumination focus (together with the detection optics) determines the axial resolution of the final image. As a result, OLM is excellent for is well-suited for high-resolution imaging, such as, for example, functional imaging. For example, OLM's resolution can be subcellular, and is the same as the high resolution of standard confocal/two-photon microscopes. OLM is also ideal for use with fluorescent and other emitting markers, such as for example, markers to label gene expression like antibodies, genetic reporters, nucleic acid labels, quantum dots, etc. In addition, particularly for imaging 3D biological samples, illumination in OLM is limited only to the plane that is being imaged, hence reducing photobleaching and phototoxicity; detection is done in parallel for the whole plane, usually with a CCD camera, hence time acquisition is fast.

Because of these inherent advantages, conventional OLM has been the subject of intensive study, and the literature discloses many recent implementations of the conventional OLM technique. (See Huisken and Stainier, referenced above.) Some of these techniques include Orthogonal Plane Fluorescence Optical Sectioning (OPFOS), Selective Plane Illumination Microscopy (SPIM), Ultramicroscopy, Digital Scanned Laser Light Sheet Fluorescence Microscopy (DSLM), Multi-Photon OLM, etc. Although these different implementations have different specialized features, they have one common critical feature: the illumination is done with a sheet of light orthogonal to the detection direction. In the DSLM technique, the light sheet is synthesized by scanning, via a movable device such as a galvanometer mirror, a low-NA focused beam of light. Seen from the side through the detection objective, the focused beam of light appears as a line of light. At any time instant the sample is illuminated by only a line of illumination, which when summed over the scanned space and over time, yields an illuminated light sheet. In multi-photon OLM, a multi-photon (MP) excitation is used to produce the emitted radiation signals, which could be, but are not restricted to, fluorescence, second harmonic generation, third harmonic generation, sum frequency generation, and stimulated Raman scattering. Using such MP excitations can help to mitigate the detrimental effects of scattering/refraction in samples, biological or non-biological (U.S. Patent Pub. No 2011-0122488, the disclosure of which is incorporated herein by reference. It should be understood that any of these conventional OLM techniques may be incorporated into the device of the current invention.

Inventive OLM/COT Microscopy

The current invention describes an imaging apparatus capable of three-dimensional volume imaging that can operate simultaneously in both OLM and COT modes. As described above, each imaging modality (OLM & COT) provides different, and complementary, functionalities, similar to transmitted versus epi in confocal laser scanning microscopy. For example, OLM is ideal for functional imaging and subcellular resolution, and because of its orthogonal geometry operates best with fluorescent and other emitting contrast markers, while COT is ideal for structural imaging and identifying features at the organ or tissue level, and because of its transmissive geometry is ideal for use with absorptive or transmission contrast markers. Accordingly, a biomedical research laboratory would ideally like to have access to both types of microscopy, allowing access to the widest possible information on any single sample. However, there is a high cost, both in monetary and space-related terms, associated with owning two different microscopes in order to do both OLM and COT microscopy. In addition, for imaging large biological samples, parallelization in both illumination and detection is critical to correlate the data obtained.

Figure 3:
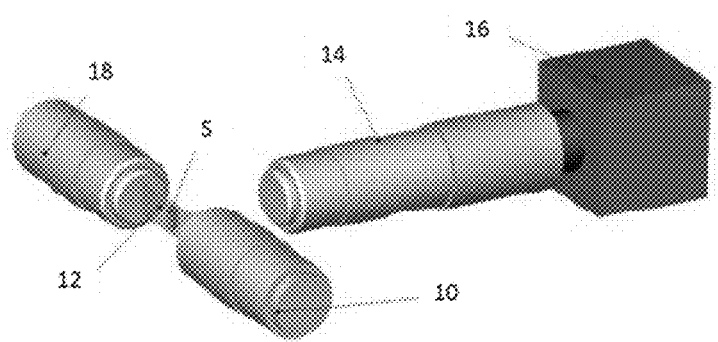
FIG. 3 provides a schematic arrangement of the excitation and imaging objectives for a dual-mode microscope in accordance with an embodiment of the invention.

The current invention specifically deals with using a novel optical arrangement to allow for the coexistence of the OLM and COT modes of operation in the same imaging instrument. An embodiment of the combined OLM/COT microscope is shown schematically in FIG. 3 (perspective view). As seen, the microscope consists of an OLM excitation objective (10) that produces an two-dimensional sample excitation beam or region having an effectively uniform excitation intensity or light-sheet (12) that intersects the sample (S) in the sample holder, an OLM collection objective (14), an OLM imaging detection system, such as a CCD camera, (16), and a COT collection objective (18), which is also in signal communication with a COT detection system (not shown).

In terms of geometry, the OLM excitation objective (14) and the COT collection objective (18) are on the same optical axis such that the light-sheet (12) exits from the excitation objective (10) and enters into the COT collection objective (18). The OLM collection objective (14), meanwhile, is placed orthogonal to the optic axis of the excitation objective (10) and the COT collection objective (18). The OLM detection system (16) is placed on the same optic axis as the OLM collection objective (14). The OLM objective (14) is placed a distance from the light-sheet (12) such that the fluorescent image is in focus at the imaging plane of the detection system (16). Likewise, the distance between the light-sheet (12) and the COT objective (18) should be adjustable for proper focusing and alignment of the image.

Although not shown, it should be understood that between the excitation source (not shown) and the excitation objection (10), between the COT collection objective (18) and the COT detection system (not shown), and between the OLM collection objective (14) and the OLM detection system (16) there may be placed any suitable optics, such as tube lenses or other optics to correctly size and image the light from the light sheet (12) onto the imaging planes of the detection systems. There may also be mirrors, prisms, or gratings, and the optical paths between the various elements behind the various objectives may not be straight linear paths.

Turning to the individual components of the device, they include:

Excitation objective lens. This is the optical component that takes in the excitation light and produces a planar light sheet (12), along the x'y' plane, at the sample position. For the basic design, a standard microscopic objective could be used. Different, more specialized optical components and/or combinations could be used here to create the light sheet at the sample, e.g. cylindrical lenses, axiconic lenses (to create Bessel beams), etc. Some of these alternatives will be described in greater detail in the alternative embodiments below.

Sample chamber. This is made of a suitable material and design for the sample and the imaging application. For example, if the sample needs to be in water, then (5) has to be water-tight, with optical access windows. If water-immersion objectives are to be used, then appropriate water-sealing features have to be implemented. Sample chambers suitable for microscopy have been described in the literature. (See Huisken, J. & Stainier, D. Y. R., *Development* 136, 1963-1975 (2009), the disclosure of which are incorporated herein by reference.)

Sample holder and controller. Similar to the sample chamber, these should be made of a suitable material and design for the sample and the imaging application, and have been described in the literature. The sample may be fixed or live, and should be held at a designated spatial location. The controller must be able to move the sample with high accuracy and precision to orient the sample within the field of view, and must be able to move the sample relative to the focal plane of the OLM and the scanning plane of the COT in order to reconstruct the volume. These motions should include linear motion in all three dimensions as well as rotational movement, and must be repeatable and accurate to the resolution of required in the z-stack (typically a few μm or less).

The sample itself may be embedded in a matrix medium to prevent motion drift. Alternatively, the sample may be fixed to a rigid, artificial tether or support to prevent motion drift. The key characteristics of an appropriate support matrix are:

correct rigidity, rigid enough to prevent motion drift, but compliant enough to allow for organism cell growth and cell division/multiplication;
optical compatibility;
bio-compatibility; and
permeability (related to bio-compatibility).

More specifically, if a support matrix is used, it must be compatible with sample and imaging contrast agents, should not distort the sample tissue, and should not extract or damage contrast agents such as dyes or fluorescent proteins. Preferably, the support matrix should have little or no contribution to the detected signal, and it should be invisible or transparent to any excitation or emission photons. For live tissue samples, support matrix should provide correct conditions to support life, such as air or water permeability, and be non-toxic. Again, preferably the support matrix would be index matched to the imaging environment, such as air or water or immersion oil. Finally, the support matrix should not inhibit growth of living tissue if growth dynamics are to be studied. Suitable examples include agarose in a water environment with water dipping objectives for imaging. For example, for imaging of live fruit fly embryos, the embryos could be affixed with glue to a small (diameter ~1 mm) capillary tube, which is held vertically by a pipette holder, which in turn is held by a combination of precision motorized stages that allow control of the samples x-y-z positions and rotation around the x' axis. Although so far only biological samples have been discussed, it should be understood that the same imaging instrument could be applied to image non-biological samples.

Objective lens for OLM/COT. These are the optical components through which the signals are collected. The OLM objective (14) has its optical axis orthogonal to the light sheet created by the illumination objective. The COT objective has its axis in-line with the light sheet created by the illumination objective. For samples that have to be in an aqueous medium, a water-dipping objective should be used. For certain appropriate applications, the objectives could be gel-coupled to the sample. Both the illumination and detection objectives should be mounted on appropriate stages with adjustable x, y, z, tip, tilt, roll (or any subset of these), to facilitate confocal orthogonal alignment of the two objectives at the sample area. It could also be useful to mount the detection objective on motorized stage that can be moved along its optical axis (the z' direction).

OLM/COT Detectors. The image created at the sample by the light sheet is captured by the detector. In choosing a suitable detector for both the OLM and COT microscopy, close attention should be paid to make sure the specifications of the detector (frame rate, quantum yield, read noise, etc.) match those required by the imaging applications. For example, both COT data and OLM data may be taken with an area detector, or they may be directed to linear detector arrays. Alternatively, the COT and OLM data could use different types of detector systems. Depending on the wavelength of the emission light that is being recorded, appropriate optical fillers or monochromators (spectral or spatial/fixed or tuned) can be placed before the camera to allow only the right wavelengths to pass through. In addition, a mirror may be used to direct light to the detector, including back through the objective. Emissions of different wavelengths could also be separated and recorded separately with multiple cameras, using any of the many widely known optical spectral separation techniques. It should be understood that the emitted light detected may include, but not be limited to, fluorescence, scattered excitation light, and Raman-shifted scattered light.

The dual-mode microscope may include one or more laser light sources, to be shared between the OLM and COT imaging modes. Although any light source suitable for exciting a sample in both OLM and COT modes may be used, in a preferred embodiment the device incorporates at least one continuous-wave laser with wavelength in the visible range (approximately 400-700 nanometers), and at least one pulsed laser with wavelengths in the near-infrared (NIR) range (approximately 700-1400 nanometers). The pulse duration of the pulsed-laser could be in the nanosecond, picoseconds, or femtosecond range. The continuous-wave laser light source(s) would produce one-photon-excited signal contrast, such as, but not limited to, one-photon-excited fluorescence, Rayleigh scattering, Raman-shifted scattering. The pulsed light source(s) would produce multi-photon-excited signal contrast, such as, but not limited to, two-photon-excited fluorescence, second harmonic generation, sum frequency generation, stimulated Raman scattering, third harmonic generation.

Operation of the Combined OLM/COT Microscope

Because in the dual-mode microscope of the instant invention the OLM objective collects light from an orientation orthogonal to the light-sheet and the COT object collects light from an orientation in-plane with the light-sheet, information from 2 types of optical contrast agents can be obtained with the inventive microscope: transmission (or reflection) through (or from) an absorptive marker and emission from an emissive marker. The emissive marker may be fluorescent (or phosphorescent), or exhibit nonlinear optical properties, such as, but not limited to second harmonic generation or 2-photon fluorescence. The operation of these two different types of markers is described below with reference to FIGS. 4 and 5.

Figure 4:
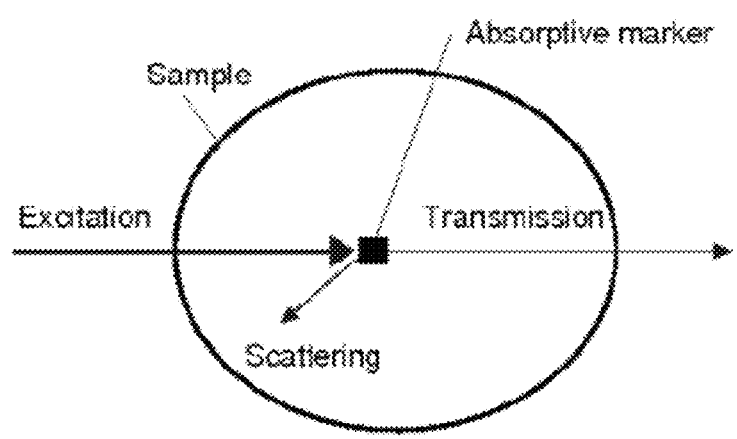
FIG. 4 provides a schematic showing excitation, scattering and transmission where an absorptive marker is used as a contrast agent in accordance with an embodiment of the invention.
Figure 5:
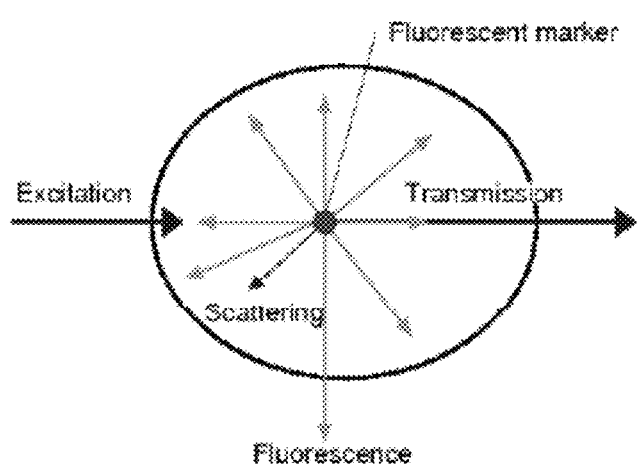
FIG. 5 provides a schematic showing excitation, scattering and transmission where fluorescence marker is used as a contrast agent in accordance with an embodiment of the invention.

FIG. 4 shows an example of the absorptive marker for the purpose of detecting transmitted light. Excitation light travels through the sample to the absorptive marker. Some of the light is absorbed by the marker, and some of the light is transmitted. (A small portion is scattered.) The amount of light transmitted describes the number of absorptive markers in the path. This information can be used to compute the original location of the markers using a method such as the filtered back projection algorithm. FIG. 5, meanwhile, shows an example of an emissive marker. Excitation light travels through the sample to the emissive marker. Some of the light is absorbed by the marker, and this light energy is then converted into fluorescence. The rest of the light is transmitted. (A small portion is scattered.) The fluorescence is omnidirectional. By using optics, the image of the original emissive markers is magnified and projected to an imaging plane, where a detection system is placed, such as electronic detectors (photo-multiplier tubes, cameras, etc.) or the human eye.

Although any suitable markers may be used with the inventive microscope, scattering should be taken into account in choosing those markers, and in particular for samples that are thicker or have greater scattering potential. For example, COT techniques operate more effectively with a clearing solution such as benzyl alcohol and benzyl benzoate (BABB) or Murray's solution to minimize scattering. Other solutions such as cedar wood oil or methyl salicylate can be also used. In the current invention these solutions could be used, or other scattering minimizing dyes and solutions might be used. For example, infrared excitation and/or infrared dyes or infrared fluorescent proteins could be used, because IR gives better depth due to less scattering, but the diffraction-limited resolution is larger due to larger wavelength. Near-infrared (NIR) markers might also operate for COT. The limitation or lack of NIR fluorophores or fluorescent proteins might be circumvented by using 2-photon techniques, as will be discussed in greater detail below.

Regardless of the type or types of markers used, to take advantage of the capabilities of the inventive microscope, it is necessary to modify the manner in which COT data is collected. As shown and discussed above with respect to FIG. 2A, for conventional COT techniques the entire sample is illuminated by the excitation light simultaneously. This is done for several rotations and the resulting information is used to compute the 3-dimensional image. In contrast, the method for acquiring optical data from a sample with the inventive microscope is different than the standard OPT technique because one plane is imaged at a time instead of the whole projection, as shown schematically in FIGS. 6A to 6C.

Figure 6:
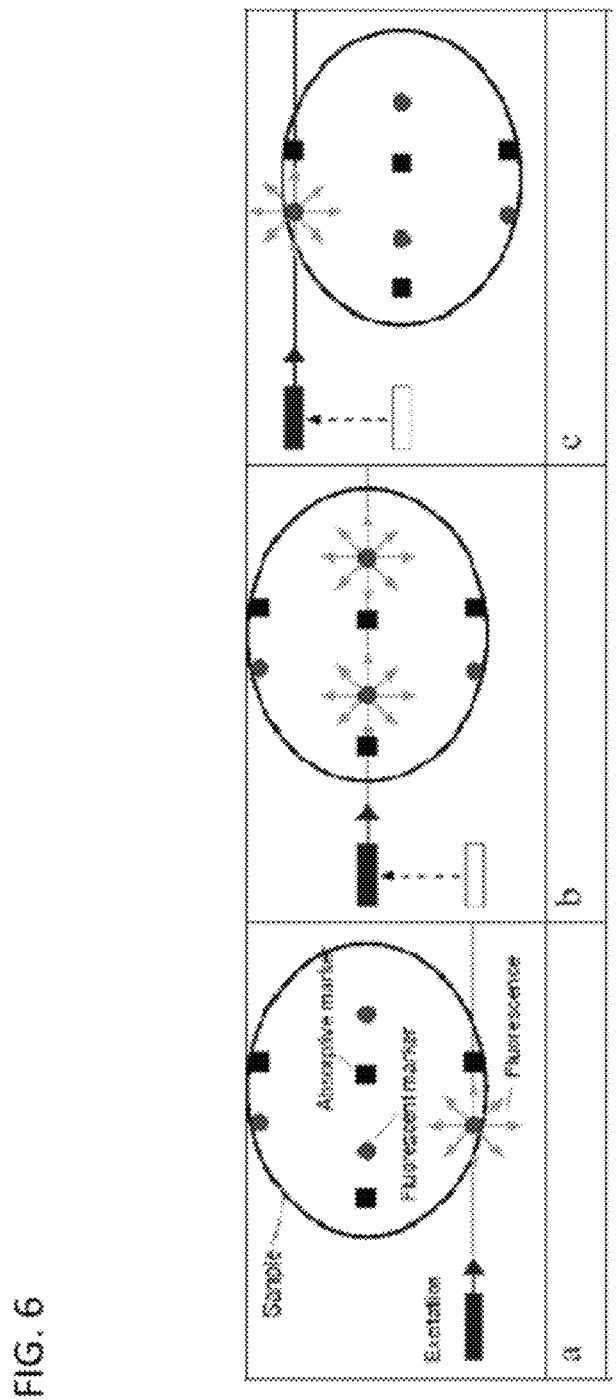
FIGS. 6a to 6c provide schematics showing the steps to collect data for OLM and COT in accordance with the current invention.

As seen, in the inventive method a sheet of light is generated and passes through a slice of the sample as shown in FIG. 6A. This light causes excitation of emissive markers, such as fluorescent markers, and is also absorbed by absorptive markers. The emission is collected by the OLM collection objective (element 14 in FIG. 3) and transmitted to the OLM imaging detection system. The light that passes through the sample containing information about the absorptive markers is collected by the COT collection objective (element 18 of FIG. 13). After this information is collected, the light sheet is translated relative to the sample as shown in FIG. 6B. It should be understood that the light sheet can be moved and the sample kept stationary, or the light sheet can be fixed and the sample can be moved. Regardless, a new plane is illuminated and the corresponding data is recorded. This is continued until the last plane is illuminated and recorded as shown in FIG. 6C.

Figure 7:
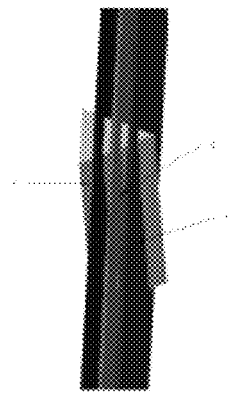
FIG. 7 provides a schematic of the z-stack sheet scan in accordance with the current invention.

FIG. 7 shows this collective process schematically from another perspective. In summary, in this embodiment, the light sheet is scanned sequentially from position 1 to position 2 to position 3 to build the 3D volume image. In the final implementation, the light sheets will be spaced apart by a variable distance depending on desired resolution. For full resolution, the distance between subsequent light sheets should be half the thickness of the light sheet at the thinnest point, the beam waist for a Gaussian beam.

Figure 8:
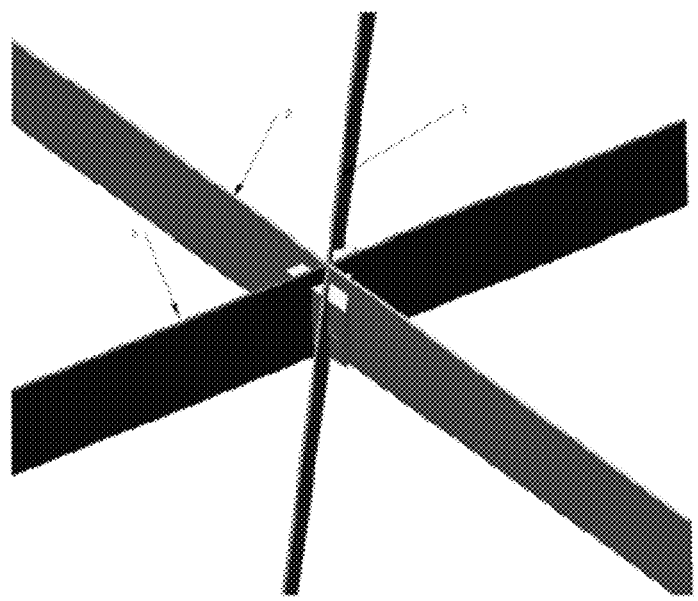
FIG. 8 provides a schematic showing rotation of the sample with respect to the light sheet orientation to capture multiple projections in accordance with the current invention.
Figure 9:
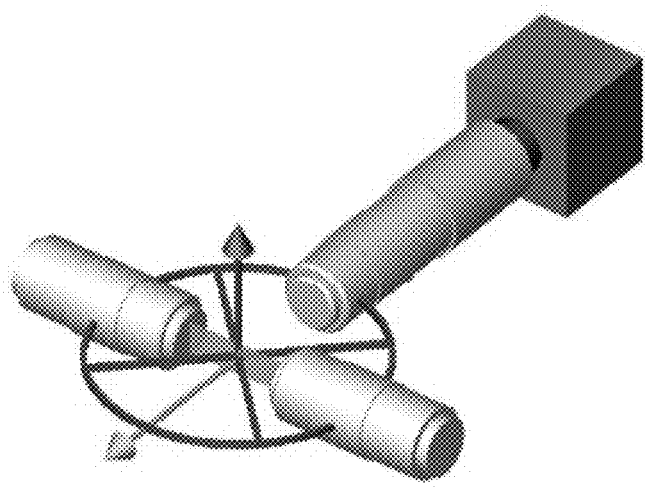
FIG. 9 provides a schematic showing an embodiment for rotating the sample relative to the light sheet axis with the axis of rotation perpendicular to the axis of the sheet scanning.

In addition to stepping through the sample plane-by-plane, COT requires imaging the sample from various rotational angles as shown in FIG. 8. There are two possible methods of capturing all the information, which are shown schematically in FIGS. 9 and 10. In summary, there are two relevant axes, the "rotation axis", which is the axis around which the COT is measured, and the "Z-scan axis", which is the axis along which the OLM is scanned. The microscope of the invention can be operated such that the rotation and Z-scan axes are either be parallel or perpendicular, however, the axis of rotation should not be parallel to the OLM excitation axis.

In a first embodiment these axes are perpendicular. In this method all the OLM data is obtained for a volume at a fixed sample rotation along with partial COT data and then the sample is rotated. For example, as shown schematically in FIGS. 8 and 9, the sample is first imaged at orientation for light sheet 1. After a full stack is acquired (as shown schematically in FIG. 8), the sample is re-oriented such that the light sheet sample angle is as shown by light sheet 2. Another full stack is acquired before another rotation such that the orientation is as shown by light sheet 3. Using this method allows the OLM scan to incorporate multiple rotation views, which improves resolution. For example, it has long been known that providing front and back views improves OLM performance, but the additional views afforded by this method will further improve resolution. Accordingly, this perpendicular mode can be used for higher resolution OLM, but the COT data acquisition rate is much slower.

Figure 10:
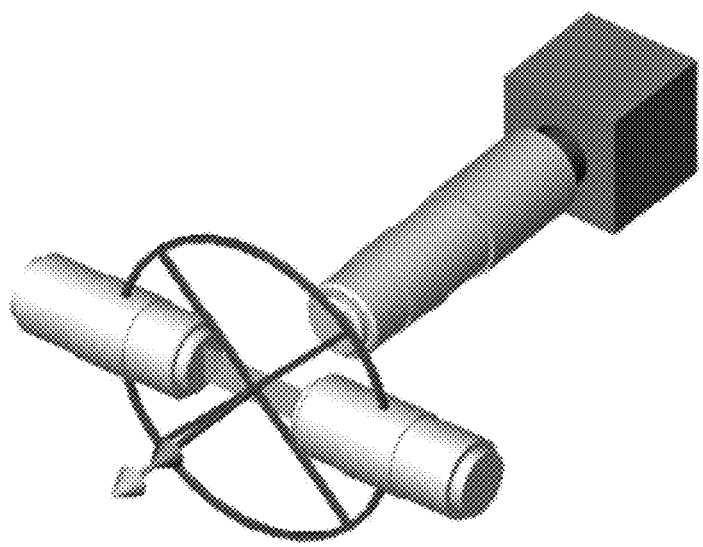
FIG. 10 provides a schematic showing an embodiment for rotating the sample relative to the light sheet axis with the axis of rotation parallel to the axis of the sheet scanning.

In a second embodiment the Z and rotational axes are parallel. In this method all the COT data is be acquired for the illuminated plane by rotating the sample about the axis of OLM imaging, as shown in FIG. 10. Then the illuminated plane is stepped before repeating the process. In this parallel method, OLM and COT can be timed to finish simultaneously, but it does not give the same multiple views of OLM as the perpendicular method.

In either method, COT requires rotation over 180 degrees, in steps of a specified number of degrees for best resolution if the illumination is symmetric with respect to axis of rotation, and requires rotation over 360 degrees, in steps of a specified number of degrees, for best resolution if the illumination is asymmetric with respect to axis of rotation. In the preferred implementation, the angles between the light sheets should be small enough such that the COT reconstruction will have enough resolution (typically less than 1 degree). Alternatively, COT could be performed with less than the ideal number or degree of rotations, and though this method might not provide enough information for a full reconstruction, it could still provide useful context information in combination with the OLM data.

Finally, it should be understood that in either method the sample could be fixed and the objectives could be rotated, or the objectives could be fixed and the sample could be rotated without impacting the operation of the inventive microscope. Likewise, as long as the relative orientations are kept fixed, the whole apparatus can be aligned arbitrarily relative to the gravitational axis.

By using either of these methods, simultaneous OLM and COT data can be collected. It should be understood that the OLM and COT data acquisition do not have to be done simultaneously in the device (like confocal and/or 2-photon imaging on traditional microscopes). However, there are a number of advantages to doing simultaneous OLM-COT, the principle being that by combining OLM and COT simultaneous data can be collected. This is important in a number of contexts:

In many applications it is necessary to have structural imaging (from COT) to give context to the functional imaging obtained via OLM.

Different dyes or combinations of dyes can be used. For example, COT doesn't need an external dye, natural contrast could be used. Alternatively, because COT is used absorptive, transmissive or reflective contrast agents could be used.

Detection of orthogonally scattered excitation light can be used to capture otherwise undiscoverable information, like in traditional dark-field microscopy.

The inventive microscope is a step towards the collection of all photons emitted in all directions, and the more photons collected the better due to signal-to-noise and information content.

Beyond the structural/functional synergy of OLM and COT there can be other correlations, such as, for example, without dyes or fluorescent tags (using autofluorescence and detecting the excitation wavelength to look at scattering), the slope of excitation absorption could be obtained to correct for non-uniform OLM illumination, and dark spots from OLM may allow for the reduction in the linear integration of COT to a piecewise integration with certain portions set identically to zero.

Moreover, from a practical standpoint, there are a number of additional advantages:

Because both techniques require rotation of the sample it does not impact the actual operation of either technique.

By combining the techniques it is possible to use the otherwise unabsorbed and unused excitation beam for COT reconstruction, and because fluorescence is captured orthogonally by OLM unwanted excitation signal is removed.

It allows true parallel microscopy as opposed to pixel-by-pixel raster scanning, thus area or linear/array sensors could be used instead of a single detector or PMT.

Additional Features

Although, the above describes the basic optical arrangement of the invention, it should be understood that other features maybe added to this basic design. In particular, the optical space between the OLM objective (14) and the detection system (16) provides a convenient space for addition of different optional components (see below) to add features to the OLM module.

Additional features for the OLM module include (but are not restricted to): multi-photon excitation, shutter to control illumination, bidirectional illumination, multi-angle illumination, bidirectional detection, structured illumination, cylindrical illumination lenses, headstage with eyepieces for direct viewing, detection optical filters, spectral separation of the emitted light (via dichroic beamsplitters and bandpass filters) to allow simultaneous detection of different wavelengths, anisotropic. Several of these key features are described below.

Multi-photon Excitation

The literature discloses a technique that reduces the detrimental effect of scattering/refraction to imaging: multiphoton (MP) excitation. In standard single photon (SP) excitation, one photon of the illumination light interacts with the sample and gives rise to an emitted photon (usually in the form of fluorescence). In MP excitation, the excitation step involves n number of photons, where n is equal to or greater than 2. The multiple number of photons interact with the sample essentially simultaneously, and then give rise to emitted radiation, which could be in the form of fluorescence, second harmonic generation, third harmonic generation, etc. (See, J. Pawley, *Handbook of Confocal Microscopy*, 3rd Edition, New York: Springer (2006), the disclosure of which is incorporated herein by reference.) For MP excitation, the excitation probability, and hence the emitted signal., is proportional to $I^n$, where I is the instantaneous intensity of the laser light at the sample. This can be contrasted with the SP case, discussed above, where the signal is proportional to I.

In carrying out the MP excitation, any suitable source of excitation energy may be utilized, however, in a preferred embodiment pulsed lasers are used in order to achieve the high instantaneous intensities required to produce significant levels of emitted signals (which are proportional to $I^n$ for MP excitation processes). The pulsed lasers can be of any suitable type, such as, for example, nanosecond, picosecond, or femtosecond-duration pulses. The shorter the pulse, the lower the total laser energy is needed to achieve the same level of instantaneous intensity. In light of this, for biological samples, in order to minimize thermal damage, femtosecond pulses (with duration of hundreds of femtosecond or shorter) are preferred. In turn, picosecond and nanosecond pulses might be more appropriate for non-biological samples, where thermal damage is less of a concern.

Scanned Light Sheet

Although a static light sheet may be used with the OLM module of the current invention, by utilizing a cylindrical lens and appropriate apertures in the optical relay, (see, J. Huisken & D. Y. R. Stainier, *Development* 136, 1963-1975 (2009), the disclosure of which is incorporated herein by reference.) in the preferred embodiment the illumination light sheet is created by the fast lateral scanning along a plane direction of the spherically-focused laser light (i.e., the y axis), generating a scanned sheet along a second plane (i.e., the xy-plane, perpendicularly to the z detection axis). (See, Keller, P. J., et al., (2008), cited above.)

A scanned light sheet can be generated by fast scanning of the beam, with a period of 1 ms to cover the full field of view (FOV). This kHz-speed is fast enough to produce an effectively uniform illumination intensity across the y-extent of the FOV, for imaging exposure times of tens of ms or more. For shorter exposure times, faster scanning hardware could be employed (e.g. resonant scanners or spinning polygon mirrors can scan in the range of 10-100 kHz). In this embodiment, the lateral extent of the illumination focus spot determines the thickness of the scanned light sheet, while the confocal parameter of the focal region (the distance over which the lateral extent remains less than two times its smallest value) determines the imaging field of view.

The scanned sheet feature provides dramatic and unexpected improvements in imaging capabilities over the conventional static sheet, which is typically produced by focusing through a cylindrical lens. In short, the implementation of the light sheet via fast scanning of a spherically-focused light beam achieves higher excitation power throughput, better light spatial uniformity along the vertical dimension of the FOV, and allowing convenient execution of non-coherent structured illumination to improve signal contrast. (See, Keller, P. J., (2008); and Keller, P. J. et al., *Nat. Methods* 7, 637-(2010), the disclosures of each of which are incorporated herein by reference.) In addition, it has been recently demonstrated that the scanned light sheet minimizes scattering artifacts compared to the static light sheet illumination used in SPIM. (See, Fahrbach, F. O., et al., cited below.) For multi-photon-excited signal contrast, the scanned sheet, with its instantaneous line illumination providing an additional dimension in focusing as compared to a static sheet, yields higher illumination intensity and hence higher signal levels (for the same total illumination light power).

Bidirectional Illumination

To increase the field of view of OLM, the illumination may be done from opposite sides of the sample. In this embodiment, the illumination beams from the +x and −x directions are adjusted so that their fields of view slightly overlap at the center of the sample, effectively doubling the final field of view. (See, Huisken, J. & Stainier, D.Y.R., *Opt. Lett.* 32, 2608-2610 (2007), the disclosure of which is incorporated herein by reference.) With a bi-directional optical setup, or any other that is optically equivalent, sequential illumination from opposite directions of the sample is achieved by controlling the shutters, preferably through computer control and coordinated with camera image capturing. Sequential bidirectional illumination helps to create a larger and more uniform illumination area at the sample, and bidirectional excitation is particularly preferred for multi-photon application, because in the case of MP-OLM, because the signal is spatially confined due to its $I^n$ dependence, the illumination from opposite could be done concurrently, saving in time acquisition and complexity of data acquisition controls. The resulting image would then have about twice the field of view, with the same resolution and contrast as illuminated from one side at a time.

The key design points of the setup s the use of (i) a beamsplitter, and (ii) shutters to produce sequential illumination from opposite directions. Opening/closing of shutters do not affect the propagation direction of optical beams, thus ensuring optimal alignment. One type of beamsplitter that could be used is the broadband (or for whichever appropriate illumination wavelength), non-polarizing type. Another type of beamsplitter that could be used is the polarizing type, in which case a means to rotate the polarization of input laser beam (e.g. a half-wave plate) is needed before the beamsplitter.

Adjustable Illumination NA:

The ability to adjust the NA of the illumination may be used to provide greater flexibility for the imaging device, since the signal depends quite sensitively to the NA, as described above. One way to achieve this is to have the illumination light go through a beam expander with adjustable expanding ratio, which then yields an adjustable illumination beam diameter, which in turns allow for fine-tuning the illumination NA.

Focal Volume Engineering:

Taking into consideration that in OLM microscopy (MP or SP), the lateral resolution of the captured image is determined by the detection optics, independent of the illumination NA; and for MP, the signal is proportional to $I^n$, it would be possible to engineer the spatial extent of the focal volume of the illumination light so that it is optimized for a particular sample.

For example, an anisotropic NA could be used for the illumination to obtain more uniform signal profile in a scattering sample, effectively increasing the depth penetration. For instance, for a particular sample, a particular $NA\_z$ is used along the z-axis for the excitation, to meet whatever specification for axial resolution that is needed. If sheet illumination is used the NA along the x-direction would be $NA\_x \sim 0$, and if standard line illumination is used $NA\_x = NA\_z$. Because of the scattering in the sample, and assuming that the center of the focal volume is significantly inside the sample, the light intensity has decreased significantly at the focal center, decreasing the signal contrast and thus also the excitation depth penetration.

This scenario can be mitigated by using NA_x>NA_z. The stronger lateral focusing takes light energy away from the right side part of the sample, where the illumination first penetrates the sample, and put it more to the left towards the focal center, increasing the signal contrast in this deeper region, hence improving the signal uniformity over the entire sample and increasing the depth penetration. The larger NA_x illuminates more of the sample laterally away from the focal center, but does not degrade the detected lateral resolution, since that is solely determined by the detection optics. And, by increasing only NA_x, leaving NA_z unchanged, in trying to get more signal at the larger depth, the optimal axial (z) resolution may be maintained.

Anisotropic NA could also be done with NA_x<NA_z, to have less peak excitation intensity, to reduce supra-quadratic photodamage. In general, lower NA_x reduces supra-quadratic photodamage, but increases total light energy imparted onto sample (i.e. increases linear 1photon photodamage) and reduces signal rate as described earlier.

It will be understood that the above described anisotropic illumination NA could be produced by in any suitable way, such as, for example, two sequential., adjustable slit apertures, oriented 90 degree to each other; and beam expanders that expand each dimension independently, using cylindrical lenses. Another implementation of focal volume engineering could use a Bessel beam. The benefit of a Bessel beam compared to conventional Gaussian beam includes a larger field of view for the same sheet thickness at the center. Bessel beams would be of particular advantage for MP excitation, since the side lobes of a Bessel profile, normally a problem in imaging with 1 p excitation, would produce significantly less signal because of the nonlinear dependence of the signal on the intensity. In yet another alternative, focal volume engineering could be implemented with spatial light modulators such as, for example, liquid crystal SLM, digital micromirror device (DMD), etc.

The person skilled in the art will recognize that additional embodiments according to the invention are contemplated as being within the scope of the foregoing generic disclosure, and no disclaimer is in any way intended by the foregoing, non-limiting examples.

SUMMARY OF THE INVENTION

Accordingly, the dual-mode imaging microscope of the current invention allows for the execution of both COT and OLM imaging simultaneously in a single instrument. This novel dual-mode device will allow researchers to have access to both types of microscopy, allowing access to the widest possible selection of samples. In addition, the device will reduce the high cost and space requirements associated with owning two different microscopes (COT and OLM). Moreover, as discussed in greater detail above, there are a number of synergistic effects obtained using the OLM/COT microscope of the instant invention, including:

- More efficient use of the excitation energy, because when doing side illumination for OLM, the remaining excitation light that is not absorbed is wasted, whereas by using this for COT, it can be reharvested.
- The techniques are cooperative, because some implementations of OLM require rotating the sample, in addition to scanning the light sheet, and since sample rotation is required for COT it provides efficiencies in taking data.
- Allows for better contextualization, because if the fluorescent marker, particularly fluorescent proteins in transgenic lines are not tagging ubiquitously, OLM does not give you morphological context.
- Co-registration is simplified, because the sample does not have to be removed from the setup.
- Better imaging, because the OLM data can be used to improve the reconstruction of the image from the COT data and vice versa.

Doctrine of Equivalents

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

What is claimed is:

1. A dual-mode imaging microscope comprising:
   at least one excitation source, said excitation source being capable of producing an excitation beam, and being disposed such that the excitation is directed along at least one excitation beam path;
   a sample holder in optical communication with said excitation source such that a sample contained therein is excited by said excitation beam;
   an excitation optic capable of producing from the excitation beam a substantially two-dimensional sample excitation region having an effectively uniform excitation intensity which extends in the direction of an excitation axis of the excitation beam path and transversely thereto and intersects with at least a portion of the sample holder along a pre-determined path;
   a tomography detector configured to detect an excitation generated signal contrast from the sample holder, the tomography detector being disposed such that the axis of detection of at least one tomography detector is substantially collinear to the excitation beam;
   a light sheet microscope detector configured to detect an excitation generated signal contrast from the sample excitation region, the light sheet microscope detector being disposed such that the axis of detection of at least one light sheet detector is substantially orthogonal to the sample excitation region;
   wherein the angular orientation of the excitation region relative to the sample holder may be varied about the axis of the sample holder, and wherein the position of the excitation region relative to the sample holder may be varied along the light sheet detector axis; and
   wherein the axis about which the angular orientation may be varied is not parallel to the excitation beam path.

2. The microscope as claimed in claim 1, wherein the axis of the sample and the axis of the light sheet detector are one of either parallel or perpendicular.

3. The microscope as claimed in claim 1, wherein the excitation source is a continuous-wave laser producing an excitation beam in the visible wavelength range, said excitation source being capable of inducing 1-photon-excited signal contrast for imaging, and wherein said signal contrast is proportional to $I^n$, where I is the instantaneous intensity of the excitation beam at the sample excitation region and n is the number of photons involved in the excitation, and where n is 1.

4. The microscope as claimed in claim 1, wherein the at least one excitation source is capable of producing an excitation beam of high enough intensity to induce sufficient levels of multi-photon excitation to produce signal contrast for imaging, and wherein said signal contrast is proportional to I$^n$, where I is the instantaneous intensity of the excitation beam at the sample excitation region and n is the number of photons involved in the multi-photon excitation, and where n is greater than 1.

5. The microscope as claimed in claim 1, wherein the excitation source is a pulsed near-infrared laser selected from the group consisting of lasers having pulse durations in the range of nanosecond, picoseconds, and femtosecond.

6. The microscope as claimed in claim 1, wherein the detected signal contrast is selected from the group consisting of 1-photon-excited fluorescence, Rayleigh scattering, Raman-shifted scattering, second harmonic generation, third harmonic generation, sum frequency generation, and stimulated Raman scattering.

7. The microscope as claimed in claim 1, wherein the at least one excitation source is capable of creating two coaxial and oppositely aligned excitation beams, such that said sample excitation region is formed from the overlap of said two excitation beams.

8. The microscope as claimed in claim 1, wherein the numerical aperture of at least the excitation optic is adjustable.

9. The microscope as claimed in claim 8, wherein the adjustable numerical aperture comprises a beam expander with an adjustable expanding ratio.

10. The microscope as claimed in claim 1, wherein the numerical aperture of at least the excitation optic is anisotropic along at least two axes of said excitation beam.

11. The microscope as claimed in claim 1, wherein focal volume engineering is applied to the excitation beam to optimize for light sheet imaging.

12. The microscope as claimed in claim 11, wherein focal volume engineering is implemented using one of the techniques selected from the group consisting of having the numerical aperture of the excitation optic being anisotropic along at least two axes of said excitation beam, and having the excitation beam be a Bessel beam.

13. The microscope as claimed in claim 11, wherein the focal engineering is implemented by one or more optical elements selected from the group consisting of two orthogonally oriented sequential adjustable slit apertures, a plurality of independently expanding beam expanders, liquid crystal spatial light modulators, digital micromirror device spatial light modulators, and axiconic lens.

14. The microscope as claimed in claim 1, wherein the excitation beam is one of either substantially planar-shaped or linearly-shaped.

15. The microscope as claimed in claim 14, wherein the excitation beam is linearly-shaped, and wherein excitation optic is configured to focus and laterally scan said excitation beam along a desired axis of the excitation beam path to produce the substantially two-dimensional sample excitation region.

16. The microscope as claimed in claim 1, wherein the microscope incorporates a technique selected from the group consisting of Orthogonal Plane Fluorescence Optical Sectioning (OPFOS), Selective Plane Illumination Microscopy (SPIM), Ultramicroscopy, and Digital Scanned Laser Light Sheet Fluorescence Microscopy (DSLM).

17. The microscope as claimed in claim 1, wherein the sample holder is moveable relative to the sample excitation region.

18. The microscope as claimed in claim 1, wherein the sample excitation region is moveable relative to the sample holder.

19. The microscope as claimed in claim 1, wherein the sample contains at least one type of marker selected from the group consisting of absorptive, transmissive, reflective, fluorescent, infrared, and near infrared.

20. The microscope as claimed in claim 1, wherein the sample is fixed within the sample holder in a sample matrix.

21. The microscope as claimed in claim 1, wherein the tomography detector detects a signal contrast selected from the group consisting of transmission, absorption and reflection.

22. The microscope as claimed in claim 1, wherein the light sheet detector detects a signal contrast selected from the group consisting of scattered and emissive.

23. A method of imaging an object using a dual-mode imaging microscope comprising:
producing an excitation beam, and directing said excitation beam along an excitation beam path;
placing a sample within the optical path of said excitation beam to generate at least one signal contrast;
producing from said excitation beam a substantially two-dimensional sample excitation region having an effectively uniform excitation intensity which extends in the direction of an excitation axis of the excitation beam path and transversely thereto and intersects with at least a portion of the sample;
detecting said signal contrast along a tomography detection axis that is substantially collinear to the excitation beam;
detecting said signal contrast along a light sheet detection axis that is substantially orthogonal to the sample excitation region; and
varying the angular orientation of the excitation region relative to the sample about the axis of the sample and varying the position of the excitation region relative to the sample along the light sheet detector axis to obtain data along a specific angular and positional axis of the sample, wherein the axis about which the angular orientation may be varied is not parallel to the excitation beam path; and
repeating the steps of producing, detecting and varying until sufficient angular and positional data has been obtained.

24. The method as claimed in claim 23, wherein the axis of the sample and the axis of the light sheet detector are one of either parallel or perpendicular.

25. The method as claimed in claim 23, wherein the angular orientation of the excitation region relative to the sample is rotated through at least 180 degrees.

26. The method as claimed in claim 23, wherein the angular orientation of the excitation region relative to the sample is rotated through at least 360 degrees.

27. The method as claimed in claim 23, wherein the angular orientation of the excitation region relative to the sample is varied in steps of no greater than 1 degree.

28. The method as claimed in claim 23, wherein the excitation region is scanned across the sample at multiple points along the light sheet detector axis at each different angular orientation.

29. The method as claimed in claim 23, wherein the sample is moved relative to the sample excitation region.

30. The method as claimed in claim 23, wherein the sample excitation region is moved relative to the sample.

31. The method as claimed in claim 23, further comprising inserting into the sample at least one type of marker selected from the group consisting of absorptive, transmissive, reflective, fluorescent, infrared, and near infrared.

32. The method as claimed in claim 23, further comprising fixing the sample within a sample matrix.

33. The method as claimed in claim 23, wherein the signal contrast detected along the tomography detection axis is selected from the group consisting of transmission, absorption and reflection.

34. The method as claimed in claim 23, wherein the signal contrast detected along the light sheet detection axis is selected from the group consisting of scattered and emissive.

35. The method as claimed in claim 23, further comprising focusing and laterally scanning said excitation beam along a desired axis of the excitation beam path to produce a substantially two-dimensional sample excitation region having an effectively uniform excitation intensity which extends in the direction of an excitation axis of the excitation beam path and transversely thereto and intersects with at least a portion of the sample.

36. The method as claimed in claim 23, wherein at least one excitation beam is produced with a continuous-wave laser producing an excitation beam in the visible wavelength range, said excitation source being capable of inducing 1-photon-exicted signal contrast for imaging, and wherein said signal contrast is proportional to $I^n$, where I is the instantaneous intensity of the excitation beam at the sample excitation region and n is the number of photons involved in the excitation, and where n is 1.

37. The method as claimed in claim 23, wherein the at least one excitation beam is of high enough intensity to induce sufficient levels of multi-photon excitation to produce signal contrast for imaging, and wherein said signal contrast is proportional to $I^n$, where I is the instantaneous intensity of the excitation beam at the sample excitation region and n is the number of photons involved in the multi-photon excitation, and where n is greater than 1.

38. The method as claimed in claim 23, wherein the excitation beam is produced via a pulsed near-infrared laser selected from the group consisting of lasers having pulse durations in the range of nanosecond, picoseconds, and femtosecond.

39. The method as claimed in claim 23, wherein detecting the signal contrast includes using a detection technique selected from the group consisting of fluorescence, second harmonic generation, third harmonic generation, sum frequency generation, and stimulated Raman scattering.

40. The method as claimed in claim 23, further comprising forming at least two coaxial and oppositely aligned excitation beams, such that said sample excitation region is formed from the overlap of said two excitation beams.

41. The method as claimed in claim 23, wherein the focusing of the excitation beam further includes adjusting the numerical aperture of a focusing optic.

42. The method as claimed in claim 23, wherein the focusing of the excitation beam further includes anisotropically adjusting the numerical aperture of a focusing optic such that the excitation beam is anisotropic along at least two axes.

* * * * *